(12) United States Patent
Fleming et al.

(10) Patent No.: US 7,624,654 B1
(45) Date of Patent: Dec. 1, 2009

(54) AUTOMATED SYSTEM AND METHOD FOR PROBE MEASUREMENT OF STACK GAS FLOW PROPERTIES

(75) Inventors: Matthew M. Fleming, Ypsilanti, MI (US); Bruce R. Devlin, Brighton, MI (US); Matthew R. Gentry, Dearborn, MI (US)

(73) Assignee: Airflow Sciences Leasing, LLC, Livonia, MI (US)

( * ) Notice: Subject to any disclaimer, the term of this patent is extended or adjusted under 35 U.S.C. 154(b) by 383 days.

(21) Appl. No.: 11/502,038

(22) Filed: Aug. 10, 2006

(51) Int. Cl.
*G01D 21/00* (2006.01)
(52) U.S. Cl. .................. 73/866.5; 73/23.31; 73/31.05
(58) Field of Classification Search . 73/863.81–863.86, 73/23.31, 861, 866.5, 31.05
See application file for complete search history.

(56) References Cited

U.S. PATENT DOCUMENTS

| | | | |
|---|---|---|---|
| 1,593,291 A | | 7/1926 | Critchlow |
| 3,784,902 A | | 1/1974 | Huber |
| 3,819,330 A | | 6/1974 | Creighton |
| 3,866,475 A | | 2/1975 | Thompson et al. |
| 3,885,437 A | * | 5/1975 | Reagan .................. 73/863.82 |
| 3,888,123 A | | 6/1975 | Kuntziger et al. |
| 3,977,249 A | | 8/1976 | Wittig |
| 3,998,102 A | | 12/1976 | Santorilla |
| 4,015,479 A | | 4/1977 | Apple |
| 4,047,437 A | | 9/1977 | Brooks |
| 4,161,883 A | | 7/1979 | Laird et al. |
| 4,209,693 A | | 6/1980 | Fite et al. |
| 4,346,609 A | | 8/1982 | Diesel |
| 4,361,027 A | | 11/1982 | Schmitt |
| 4,653,334 A | | 3/1987 | Capone |
| 4,817,293 A | * | 4/1989 | Daverio et al. ........... 73/863.85 |
| 4,856,352 A | | 8/1989 | Daum et al. |
| 4,942,774 A | | 7/1990 | McFarland |
| 4,974,455 A | | 12/1990 | McGowan et al. |
| 5,237,881 A | | 8/1993 | Ross |
| 5,394,759 A | | 3/1995 | Traina |
| 5,423,228 A | | 6/1995 | Budd et al. |
| 5,440,217 A | | 8/1995 | Traina |
| 5,488,875 A | | 2/1996 | Adair |
| 5,507,192 A | | 4/1996 | Beaudin |
| 5,635,652 A | | 6/1997 | Beaudin |
| 5,831,183 A | | 11/1998 | Baxter et al. |

(Continued)

*Primary Examiner*—Hezron Williams
*Assistant Examiner*—Nashmiya S Fayyaz
(74) *Attorney, Agent, or Firm*—George L. Boller (57) ABSTRACT

A system and method for the automated measurement of properties related to a stack gas stream, flow velocity for example. A probe assembly (24) is introduced into a stack through a test port and operated by an automated mechanism mounted on the test port to position a sensing tip (28) at various locations within the gas stream at proper yaw angle. A framework (30, 32, 34, 36) of the automated mechanism provides bearing support for the probe assembly while allowing the probe assembly to translate on the framework along an axis but constraining the probe assembly from turning on the framework about the axis. With a gripper assembly (44) gripping the probe assembly and another gripper assembly (56) released, a linear actuator (40) can move the gripper assembly (44) along the axis to translate the probe assembly on the framework. A motor (70), also mounted on the framework, can turn a pinion (66) that is in mesh with a toothed segment (64) of a ring gear (62) that attaches to the stack port so that the motor (70) can turn the framework and probe assembly together about the axis.

17 Claims, 8 Drawing Sheets

U.S. PATENT DOCUMENTS

| | | |
|---|---|---|
| 5,970,781 A | 10/1999 | Hiss, III et al. |
| 6,212,937 B1 | 4/2001 | Hubert et al. |
| 6,432,288 B1 | 8/2002 | Nielsen et al. |
| 6,516,676 B1 | 2/2003 | Mullowney, Jr. |

* cited by examiner

FIG. 11

AUTOMATED SYSTEM AND METHOD FOR PROBE MEASUREMENT OF STACK GAS FLOW PROPERTIES

FIELD OF THE INVENTION

This invention relates to a system and method for the automated measurement of properties related to a stack gas stream, flow velocity for example, using a probe that is introduced into a stack through a test port and operated to position a sensing tip at various locations within the gas stream at proper yaw angle.

BACKGROUND OF THE INVENTION

Industrial emissions to the atmosphere, such as those from powerplants that combust fossil fuels to generate electricity, are subject to governmental regulation that is enforced by the United States Environmental Protection Agency (EPA).

Pursuant to statutory authority, the EPA has promulgated regulations that are embodied in portions of the Code of Federal Regulations (CFR). Included in portions of 40 CFR are regulations pertaining to measurement of volumetric flow rate of stack gas streams. While the regulations specify acceptable methods of measurement and types of probes that are introduced into stacks through test ports in the stack walls for obtaining those measurements, they leave it to industry to design and develop equipment for use with the probes that will enable the probes to be positioned within a stack for obtaining volumetric flow rate measurements in accordance with regulations.

The availability of portable electronic data recording equipment enables stack measurement data to be efficiently recorded on-site in electronic form and then later processed into proper reporting format for demonstrating regulatory compliance. The ability to automate a method for positioning a probe within a stack while electronically recording gas stream data is obviously desirable for increasing the efficiency and accuracy with which a test is performed.

Accordingly, it has been proposed to employ a motorized mechanism for positioning a probe within a stack as shown and described in various patents and publications, such as U.S. Pat. No. 5,440,217.

EPA regulations specify several test methods (Methods 2, 2F, and 2G) using certain specified probes. For performing Methods 2 or 2G, an S-type ("two dimensional") probe is specified. For performing Method 2F, a prism head ("three dimensional") probe is specified. The probe must translate in a direction that is transverse to the direction of the gas stream that is passing upward through the stack and it must also be capable of turning about the axis of translation. Such turning is referred to as yaw nulling.

The extent to which the probe needs to be advanced depends on the stack diameter. The larger the stack diameter, the greater the distance that the probe needs to be advanced. In very large diameter stacks, multiple test ports are provided at locations around the stack to allow a probe whose range of translation cannot span the full diameter to be placed at those locations and used for testing.

Because the extended probe acts in the manner of a cantilever on whatever structure is supporting it, and because the probe must be able to withstand hostile stack environments, the typical probe will have sufficient mass that will cause the probe to droop to some extent when maximally extended. The EPA test methods specify a maximum allowable droop of 5°.

Droop can be minimized by increasing probe stiffness, but increased stiffness is apt to require that probe mass and dimensions be increased, and when that is done, the construction of the mechanism that translates and turns the probe while at the same time supporting the cantilevered weight of the probe needs to be much more substantial, not only from the standpoint of structure but also from the standpoint of more powerful prime movers that are used to translate and turn the probe.

The device shown in U.S. Pat. No. 5,440,217 comprises two arrays of roller wheels that are spaced apart along the length of the probe and that bear against the outside of the cylindrical probe wall. Three roller wheels are journaled in roller assemblies that are arranged approximately equiangular about the probe wall in a first array and are forced against the probe wall by spring washers. In the other array, there are two roller assemblies like those of the first array, while the third roller wheel is a drive roller wheel that is coupled to a motor so that by virtue of friction between that roller wheel and the probe wall, rotation in one direction by the motor advances the probe and rotation in the opposite direction retracts the probe. The motor is a stepper motor that operates in increments.

The roller assemblies containing the non-driven roller wheels mount on a cylindrical housing within which the probe translates, with the probe increasingly protruding from that housing as the probe increasingly advances, and decreasingly protruding as the probe increasingly retracts. An alternative drive for probe translation is a chain drive as shown in U.S. Pat. No. 5,394,759.

Turning of the probe about the probe axis is accomplished by a second motor, also a stepper motor, that acts on the cylindrical housing containing the roller wheels that engage the probe wall. A timing belt is trained around the outside of the cylindrical housing wall and presumably a shaft or sheave of the second motor so that when the second motor operates, it turns the probe by turning the cylindrical housing within which the probe translates. The second motor is housed at one end of an outer housing assembly, whose other end is fit and secured to a mounting ring on the stack at the stack test port. The outer housing assembly surrounds the cylindrical housing containing the roller wheels that engage the probe, for at least some of the length of the cylindrical housing.

Encoders track translation and turning of the probe. The motors are controlled by a computer that calculates the points at which the probe is to be positioned for testing and will output signals to the stepper motors for translating the probe to the desired test point and turning the probe to the desired angular orientation.

Analysis of the devices shown in the referenced US Patents discloses that a more robust automated probe would be desirable. Some aspects of the patented probes that may compromise robustness include: translational accuracy of the probe; the use of spring washers in one version to force the roller wheels against the probe wall in the apparent interest of providing adequate cantilever support, but at the same time creating additional stresses that must be accommodated by mechanical strengthening, which typically means added mass, and motor size large enough not only to move the probe but in doing so to also overcome the opposing force components of the spring washers; and the use of two housings, one within another, adding complexity and weight.

SUMMARY OF THE INVENTION

Accordingly, the present invention is directed toward an automated measuring probe having a number of features that contribute to greater robustness, to improved accuracy, ease of use, and the ability to position a larger probe over a greater distance with acceptable droop.

One generic aspect of the invention relates to an automated probe for obtaining data at various locations in a stack flow comprising a probe assembly having a sensing tip at one end. The probe further comprises structure comprising a mechanism for imparting translation and rotation to the probe assembly to enable the probe assembly to obtain data about stack flow.

The structure comprises a framework providing bearing support for the probe assembly while allowing the probe assembly to translate on the framework along an axis but constraining the probe assembly from turning on the framework about the axis. A translation-imparting mechanism is mounted on the framework and comprises a gripper assembly that can grip and release the probe assembly and a first prime mover for moving the gripper along the axis so that when the gripper assembly is moved while gripping the probe assembly, the probe assembly translates on the framework along the axis.

A rotation-imparting mechanism comprises a second prime mover that is mounted on the framework and turns a pinion that is in mesh with a toothed segment that attaches to the stack via a mounting so that operation of the second prime mover rotates the framework and probe assembly about the axis.

Another generic aspect relates to a probe assembly for use with a stack probe for obtaining data at various locations in a stack flow. The probe assembly comprises a square tube and a sensing tip for sensing pressure and temperature disposed at one end of the square tube. The square tube comprises individual square tube sections spliced together end-to-end by smaller square tube splices.

Still another generic aspect relates to a method for obtaining data at various locations in a stack flow via a probe assembly having a sensing tip at one end. The method comprises imparting translation to the probe assembly by translating the probe assembly on structure that constrains the probe assembly from rotating while allowing translation, and imparting rotation to the probe assembly by rotating the structure on which the probe assembly translates.

DESCRIPTION OF THE PREFERRED EMBODIMENT

For automating any of various known types of sensing tips, the invention provides an automated probe 20 comprising a self-contained supporting and positioning mechanism for supporting and positioning a square tube at one end of which a sensing tip is mounted. Probe 20 is adapted for mounting on a stack at a test port of the stack that is designed to allow the probe to be separably fastened to it, thereby supporting the entire probe 20 (including the probe assembly when the probe assembly is in place) on the stack. The probe assembly (to be more fully described later) comprises a square tube and a sensing tip that is compliant with 40 CFR for performing flow velocity measurements, with the sensing tip being fastened to one end of the square tube. The probe 20 can position the probe assembly in two directions, one being translationally across the stack diameter and the other being rotationally about the centerline of the probe assembly.

The automated probe 20 is arranged and constructed to allow the probe assembly to be inserted lengthwise, tip end first, into and through the probe interior in preparation for a test, and after the test, to be removed in the opposite manner.

Figure 4:
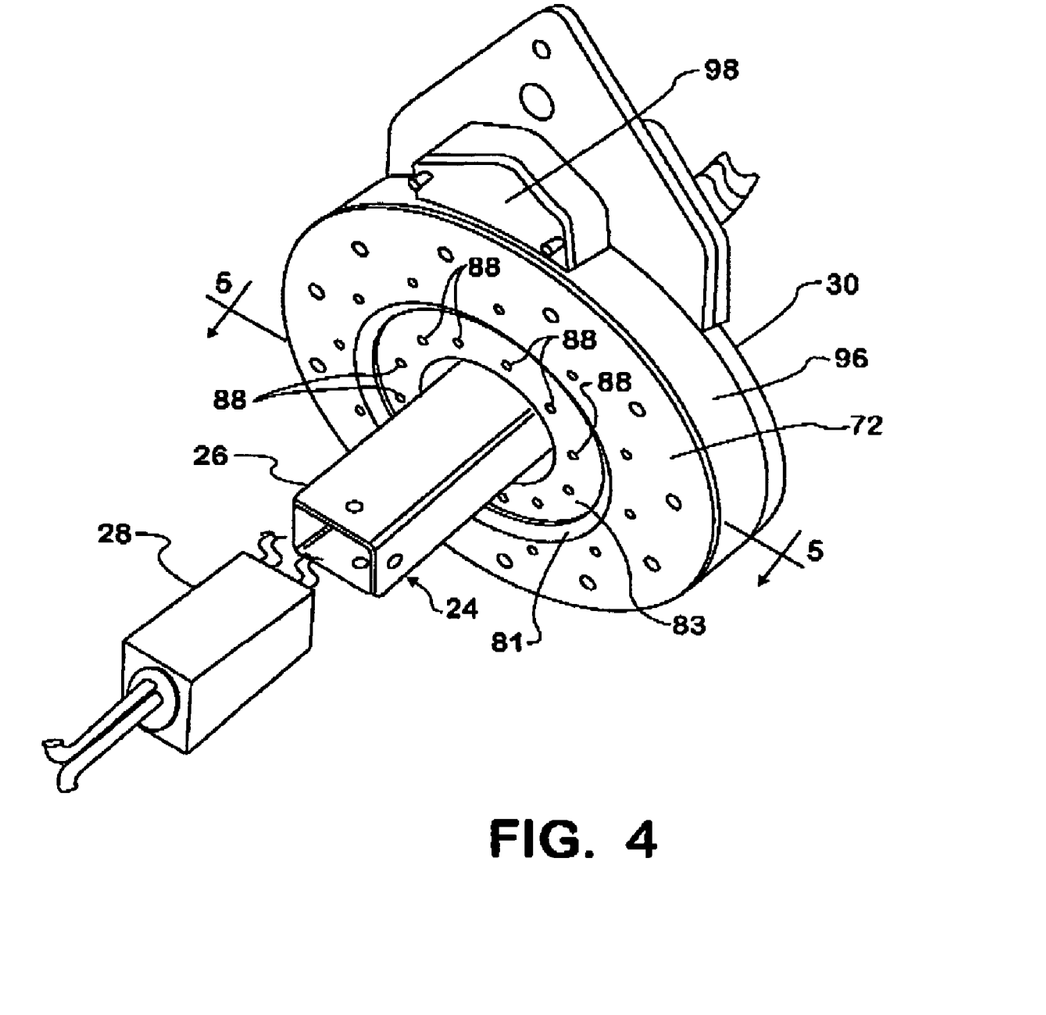
FIG. 4 is a perspective view of the same end of the automated probe shown in FIG. 2 after the probe assembly has been placed in the automated probe.
Figure 5:
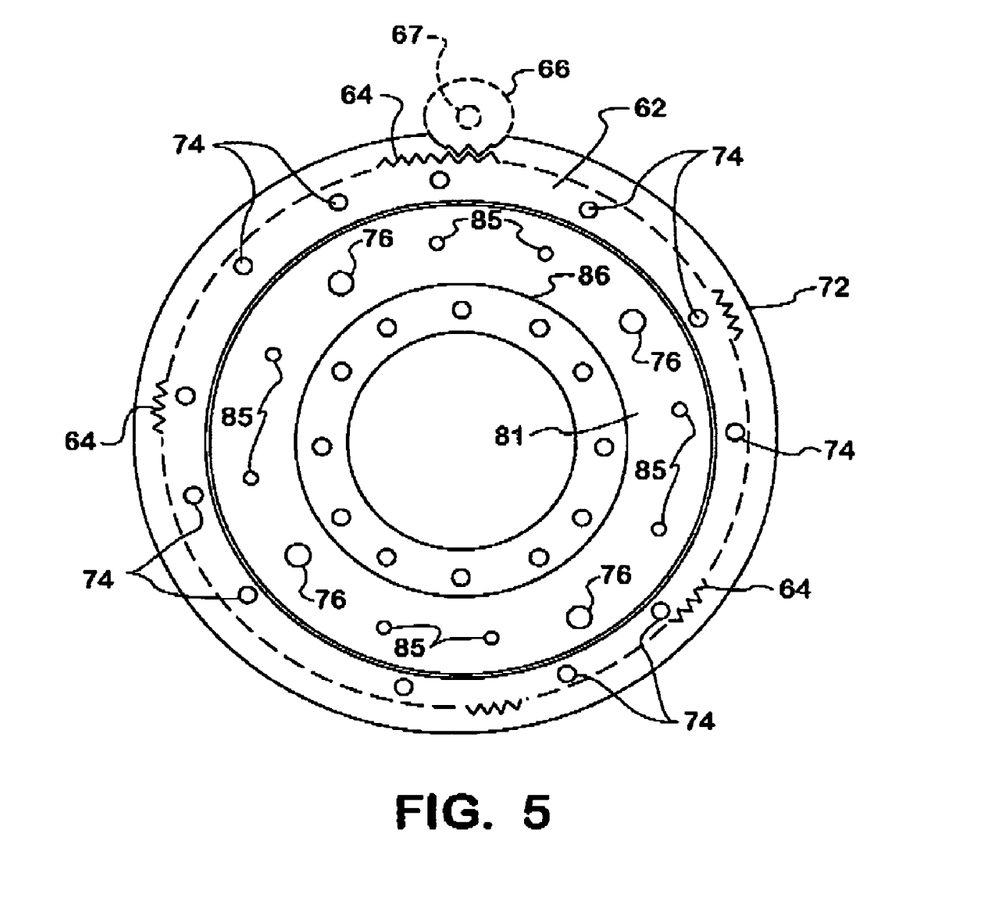
FIG. 5 is an axial view in the direction of arrows 5-5 in FIG. 4, but without the square tube of the probe assembly.
Figure 6:
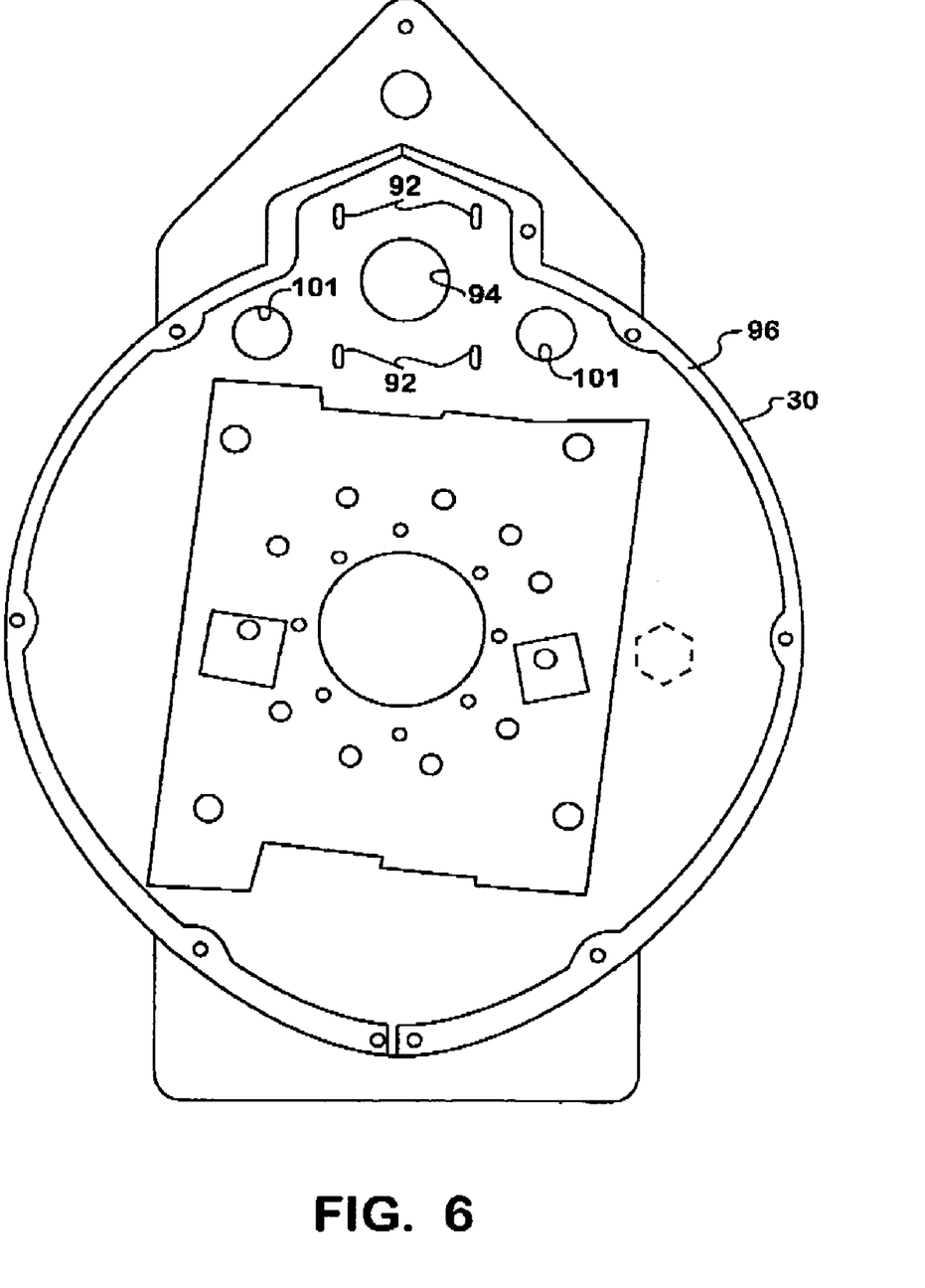
FIG. 6 is an axial view looking in the opposite direction of FIG. 5 to show one end wall of the automated probe, with certain parts omitted for clarity of illustration.

Automated probe 20 is shown in the Figures to comprise structure 22 that supports various component parts, and of course a probe assembly 24 when the latter is placed in the automated probe in the manner explained above. FIG. 4 shows probe assembly 24 to comprise a square tube 26 and a sensing tip 28 at one end.

Before a stack test, probe 20 is attached to the stack test port in a manner that will be explained with reference to FIG. 2. Probe assembly 24 is inserted, probe end first, into the open proximal (rear) end of structure 22 (right-hand end as viewed in FIG. 1, and advanced completely through that structure until the sensing tip end protrudes from the distal (forward) end, as in FIG. 4. Pressure lines from sensing tip 28 run through the interior of tube 26 and exit from the proximal end of the tube from whence they continue on to test equipment to communicate pressure sensed by the sensing tip ports to the test equipment. As also specific by EPA regulations a thermocouple mounted in association with the sensing tip is coupled to the test equipment by wires running through the square tube.

Figure 1:
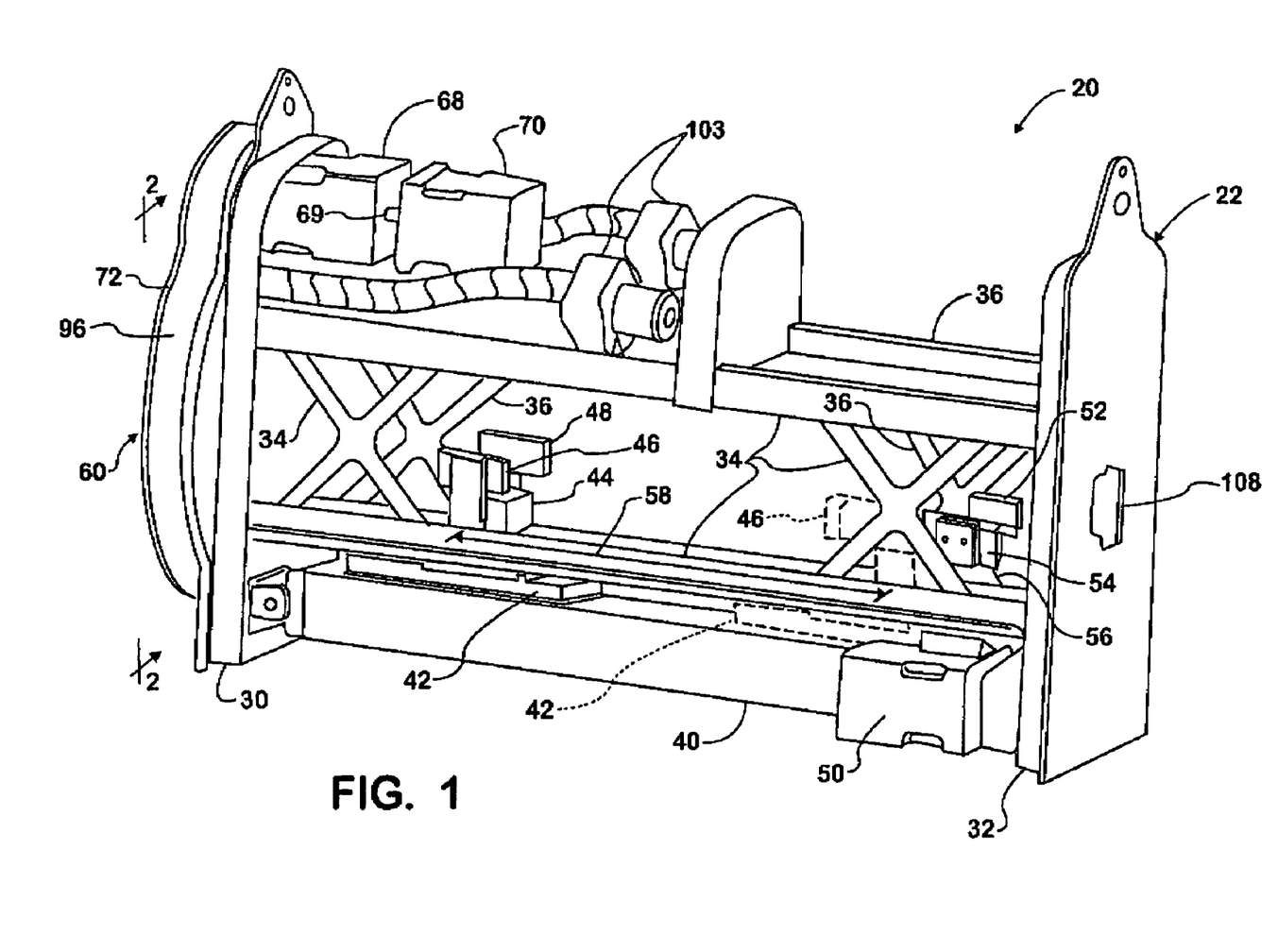
FIG. 1 is a side elevation perspective view of the interior of the inventive automated probe for positioning a probe assembly that comprises a square tube and sensing tip, but without the probe assembly being shown, and with some parts of the automated probe being omitted for clearer illustration of the parts that are shown.

At its lengthwise opposite ends, structure 22 comprises end walls 30, 32 that are joined through two rigid trusses 34, 36 that are disposed on opposite sides of the probe assembly. Extending between the end walls is a servo-motor-powered linear actuator 40 having a traveling carrier 42 to which gripper assembly 44 is attached. As actuator 40 operates, it moves carrier 42 to impart travel to gripper assembly 44.

Figure 3:
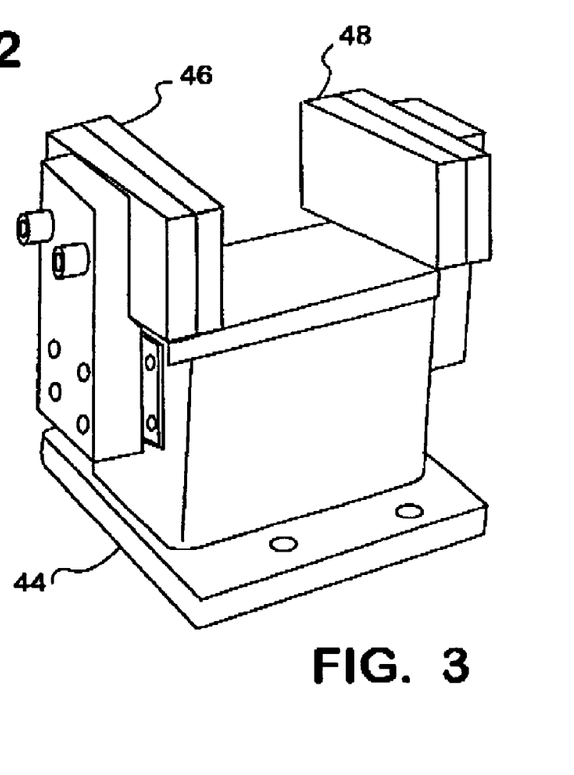
FIG. 3 is a perspective view of one of the parts shown in FIG. 1, specifically a gripper assembly.

Gripper assembly 44, shown in more detail in FIG. 3, has opposed jaws 46, 48 that confront tube 26 from opposite sides. The jaws can be opened and closed by pneumatic or electric actuation. When the jaws are operated open, the gripper assembly can travel freely with carrier 42 relative to tube 26. When the jaws are operated closed, they forcefully grip the tube sides with sufficient force to enable the gripper assembly to translate the probe assembly as actuator 40 operates, and hence move the probe within the stack. The interior of linear actuator 40 has a screw that when turned by servo motor 50 acting through a coupling to the screw, imparts travel to a nut to which the carrier is attached.

When gripper assembly 44 stops, jaws 52, 54 of a second gripper assembly 56 that are disposed on opposite sides of tube 26 can be closed to grip the tube. Gripper assembly 56 is stationarily mounted on structure 22, and thereby prevents tube translation when its jaws are closed on the tube. The jaws must be opened before the tube can be translated by gripper assembly 44.

With these elements, namely the two gripper assemblies and the motor, a sequence for translating tube 26 to position the probe assembly inside the stack can be developed. Gripper assembly 44 has a range of travel along the length of the actuator screw that is limited by suitable limit stops. One limit stop limits rearward travel of the nut and carrier, and the other limits forward travel. The range of travel is marked as 58 in FIG. 1.

With gripper assembly 44 at the rearward limit stop, tube 26 can be advanced (toward the left in FIG. 1) so as to begin extending the tube and probe into a stack during a test. The sequence comprises operating traveling gripper assembly 44 to clamp tube 26, releasing stationary gripper assembly 56 from clamping the tube, and operating servo motor 50, causing actuator 40 to move gripper assembly 44 in the direction from right (broken line position) to left (solid line position) in FIG. 1.

When gripper assembly 44 reaches the forward limit stop, the stationary gripper assembly 56 is operated to clamp tube 26, gripper assembly 44 is operated to unclamp the tube, and motor 40 is operated to move gripper assembly 44 back to the opposite limit stop (broken line position). The limit stops define a known increment of length for probe translation (range of travel 58).

The known increment of length may be chosen to correspond to the distance between consecutive locations where stack measurements are to be taken as the probe tip is positioned within the stack.

When the tube is to once again advance further into the stack, the same sequence of operations just described is repeated.

Probe 20 is particularly unique because it fastens to a mounting at the stack test port opening via a slewing ring bearing assembly 60 that is itself part of probe 20. The slewing ring assembly comprises a ring gear 62 having a toothed track 64 which runs along its outer circumference and with which teeth of a pinion 66 on an output shaft 67 of a gear reduction assembly 68 are in mesh. An input shaft 69 of assembly 68 is coupled to an output shaft of a servo motor 70. Ring gear 62 is disposed inside of a cover 72 that is fastened to the ring gear by screws 74 that thread into holes in the ring gear, with spacers (not shown) between the cover and the ring gear to space the latter from the former.

Figure 2:
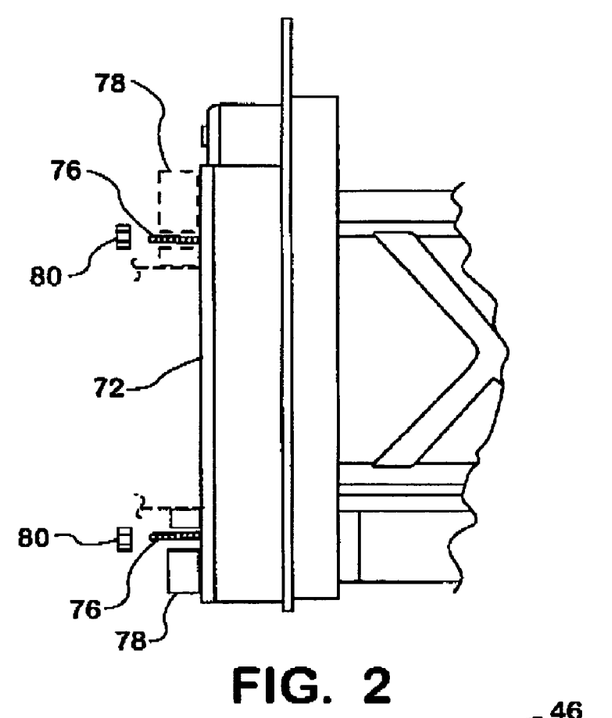
FIG. 2 is a partial side elevation view in the direction of arrows 2-2 in FIG. 1, still with some parts omitted.

Cover 72 itself fastens to the stack test port mounting via bolts 76 as shown in FIG. 2, with bolts 76 passing through holes in ring gear 62 making the ring gear stationary on the test port. The test port mounting comprises a 4 inch NSI pipe flange containing holes through which bolts 76 pass. The bolts are arranged at 90° about the probe assembly centerline. Nuts 80 are threaded onto the ends of the bolts and tightened to draw cover 72 and the ring gear inside the cover tightly against the face of the pipe flange, and consequently align the path of probe assembly travel with the test port opening.

The slewing ring bearing assembly comprises an outer race 81 that can turn on an inner race 83 via intervening bearings. It is the outer race that is fastened to cover 72 via bolts 76. The inner race comprises a ring 86 containing a number of through-holes through which screws 88 pass to fasten the ring to end wall 30.

Gear reduction assembly 68 and motor 70 are mounted on end wall 30 by four fasteners that engage holes 92. Pinion 66 is disposed on the stack side of end wall 30 where it meshes with track 64. The shaft on which the pinion is affixed passes through a hole 94 in end wall 30. End wall 30 has a side wall 96 surrounding the ring gear. Side wall 96 is nominally circular, but protrudes upwardly to partially surround pinion 66. A small cover 98 completes the enclosure of the pinion and its meshing with the ring gear.

When motor 70 operates to turn pinion 66, the entire probe, except for parts fastened to the stack mounting, cover 72 and ring gear 62 in particular, will turn about the probe assembly centerline, imparting rotary motion to the probe inside the stack. This serves to orient the probe sensing tip in yaw, positioning the probe assembly about its centerline to a position where the tip measures the maximum magnitude of the flow vector at the location to which the probe tip has translated.

Holes 101 in end wall 30 are ports for motorized blowers 103 that pressurize the interior to keep stack gases from intruding.

Figure 7:
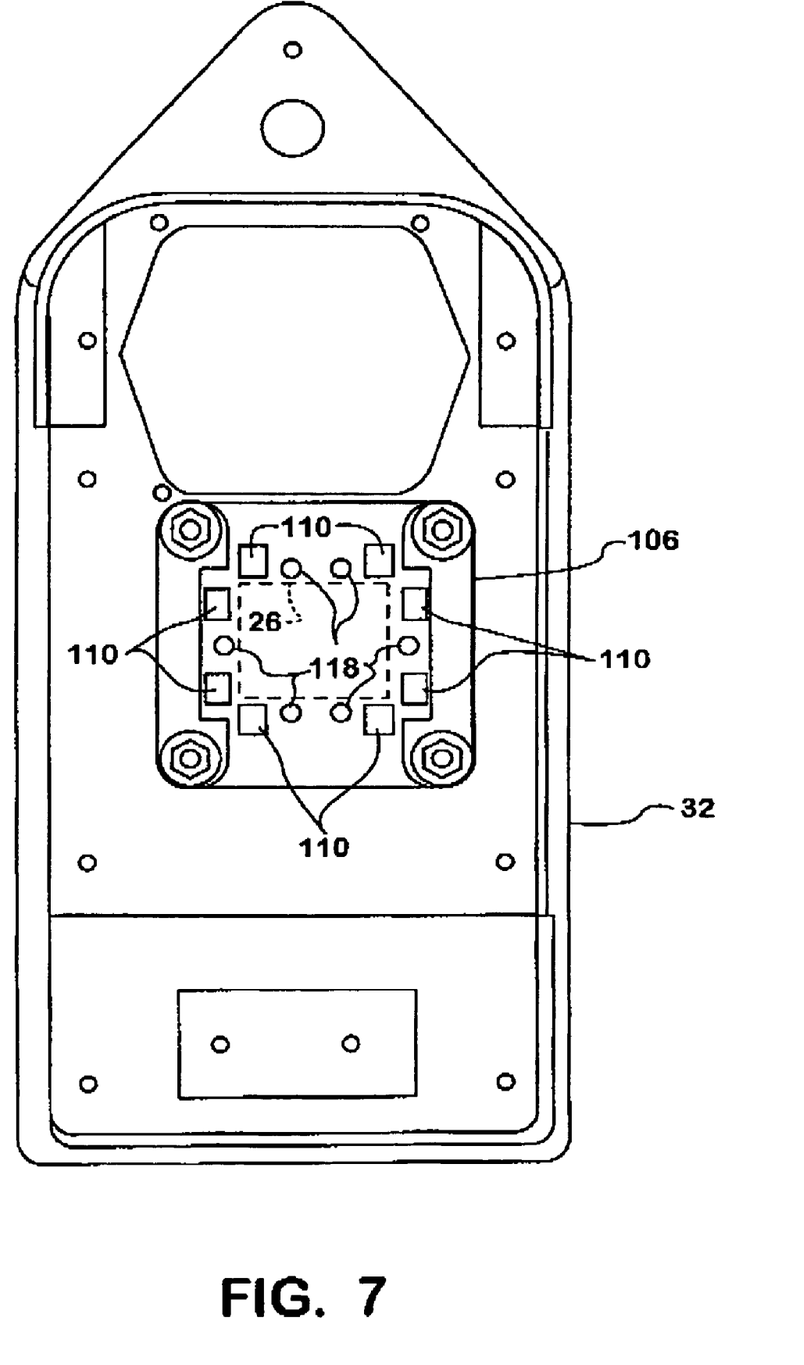
FIG. 7 is an axial view of the opposite end wall, also with certain parts omitted for clarity.
Figure 8:
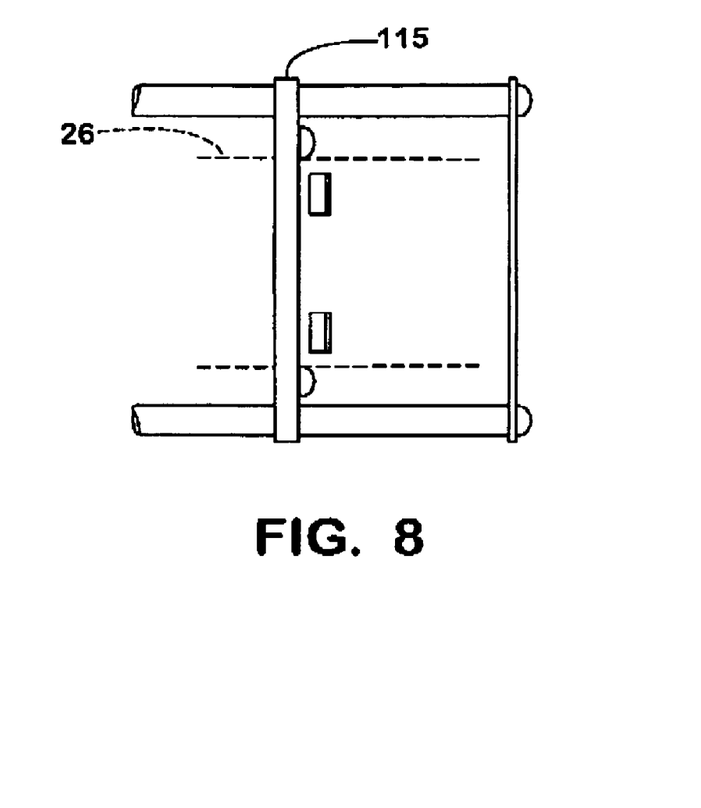
FIG. 8 is a partial side elevation view in the same direction as FIG. 2, but showing some of the parts omitted from FIG. 2.

FIGS. 7 and 8 show how tube 26 is guided and supported. A guide roller assembly 106 is fastened to the inside of end wall 32 over the opening 108 (FIG. 1) in the end wall through which the tube is introduced. Assembly 106 contains a set of eight rollers 110 for supporting and guiding tube travel within assembly 20. FIG. 8 shows a guide roller assembly 115 fastened to the opposite end wall 30. Assembly 115 is actually spaced a short distance inside that end wall. A series of circular rods 118 extend between the assemblies 115, 106 to aid in guiding tube 26 during its introduction into and passage through assembly 20 so that it will align with the rollers of assembly 115 upon reaching them during insertion of the probe assembly into and through assembly 20.

Figure 9:
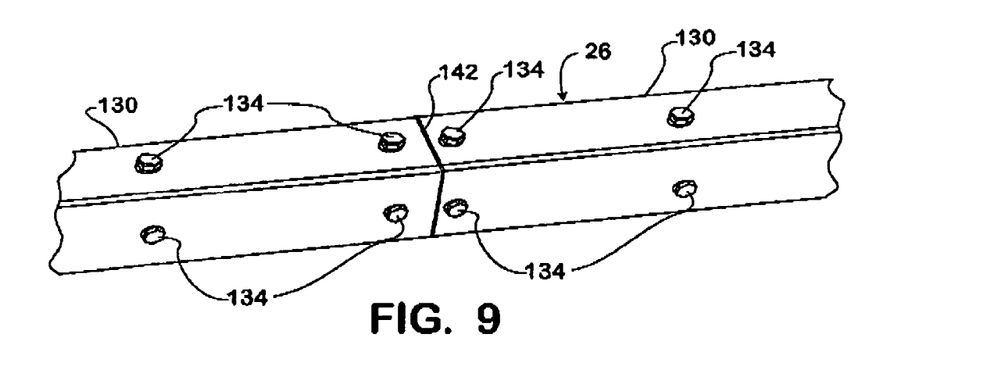
FIG. 9 is a perspective view of a portion of the square tube.
Figure 10:
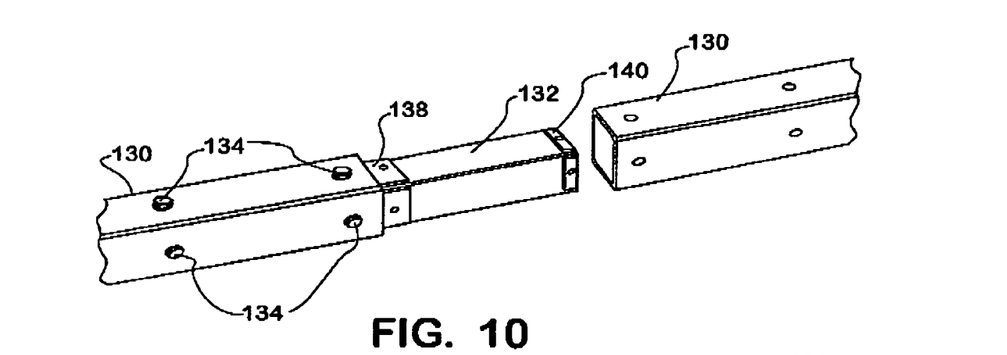
FIG. 10 is a partially exploded view of FIG. 9.
Figure 11:
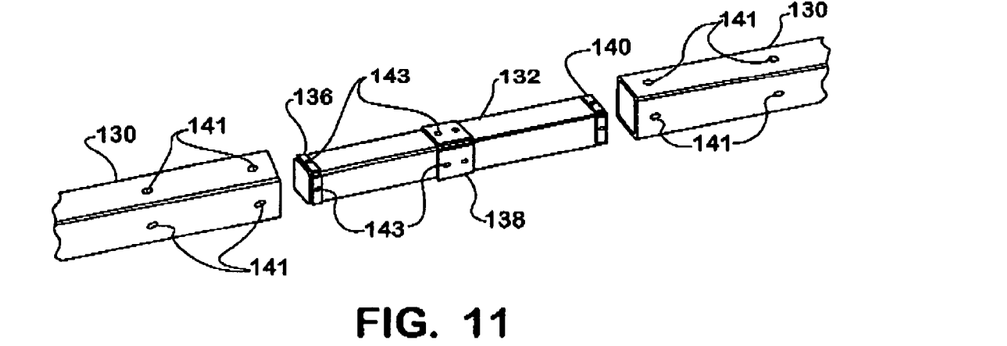
FIG. 11 is a fully exploded view of FIG. 9.

As shown by FIGS. 9, 10, 11, square tube 26 is an assembly comprising a number of individual square tube sections 130 that are connected together by splices 132 and bolts 134. Each splice 132 is itself a square tube of slightly smaller size than tube sections 130, allowing each section 130 to telescope over a splice 132 as shown.

Metal blocks are applied to the ends and middle of each splice as indicated by reference numerals 136, 138, 140. These blocks have thicknesses that make up the dimensional difference between the insides of tube sections 130 and the outsides of splices 132 so that the telescopic fit is close, yet allowing the splices to be freely inserted into the tube sections.

The end portion of each tube section 130 has a hole pattern 141 matching a hole pattern 143 in one half of a splice. When a splice has been inserted halfway into a tube section, the hole patterns register, allowing shanks of bolts 134 to be passed through the holes in the tube section and the bolts tightened in holes in the splice. Although the bolt heads are exposed, other parts of probe 20 that associate with the square tube are disposed so as not to interfere with the bolt heads. For example, along the sides of the square tube that are gripped by the grippers, the grippers can grip with sufficient force along surface zones that are below the bolt heads.

With two sections spliced together, the sections come together essentially end-to-end as marked at 142 in FIG. 9. The action of the bolt heads on the each tube section wall slightly deforms the wall along each side as the bolts are fully tightened thereby taking out any looseness in the joint. The use of square probe sections and splices also eliminates difficulties and inaccuracies of having a scribe line or other angular reference mark on sections of a round probe in order to properly align the probe sections.

Square tubes of different lengths can be readily fabricated. The use of square tube sections provides a natural passageway for pressure lines and wires from the sensing tip. And because the tube sections and splices are both hollow, a square tube provides greater strength with less weight—an efficient use of material. A square tube probe can be extended a substantial distance without exceeding droop allowed by the EPA regulations mentioned earlier.

Figure 12:
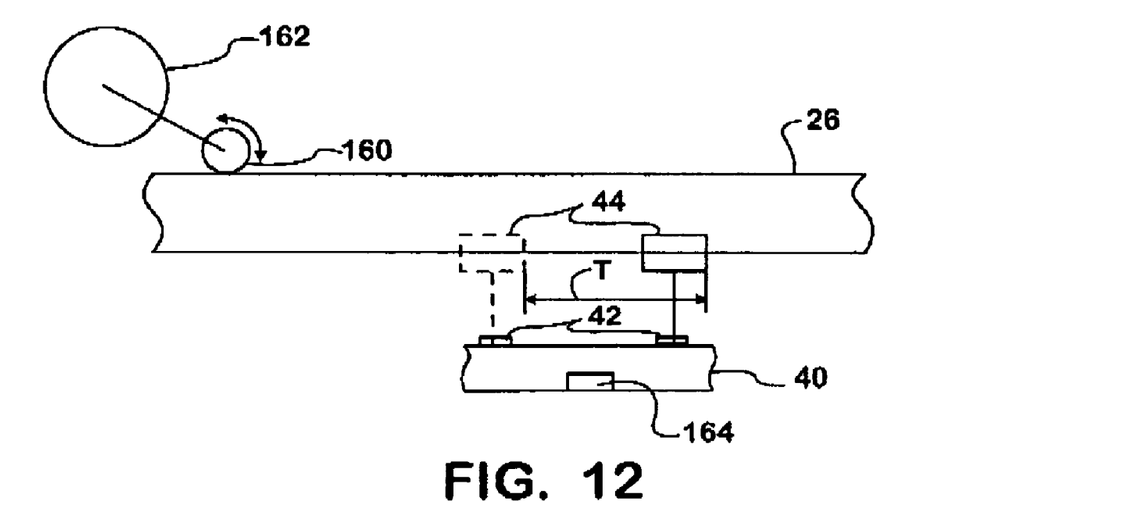
FIG. 12 is a diagram useful in explaining how probe assembly translation is measured.

FIG. 12 illustrates how translation of the probe assembly is measured. A wheel 160 is kept against a surface of square tube 26 to rotate in correspondence with tube translation. Wheel 160 is coupled to an encoder 162 which provides a signal measurement of probe translation based on wheel rotation. The signal provided by encoder 162 is used to control servo motor 50 that operates linear actuator 40 to position carrier 42.

A sensor 164 is associated with linear actuator 40 to measure translation of carrier 42 as it moves over a stroke T. By comparing measurements made by encoder 162 and sensor 164, it becomes possible to detect slippage between gripper assembly 44 and square tube 26, allowing the cause to be promptly investigated and appropriate repair made.

While a presently preferred embodiment of the invention has been illustrated and described, it should be appreciated that principles of the invention apply to all embodiments falling within the scope of the following claims.

What is claimed is:

1. An automated probe for obtaining data at various locations in a stack flow through a stack, the automated probe comprising:
    a probe assembly having a sensing tip at one end;
    structure that supports a translation-imparting mechanism and a rotation-imparting mechanism for imparting translation and rotation respectively to the probe assembly to enable the probe assembly to obtain data about stack flow, rollers disposed on the structure for providing bearing support for the probe assembly while allowing the probe assembly to translate along an axis but constraining the probe assembly from turning on the structure about the axis, the translation-imparting mechanism comprising a gripper assembly that can grip and release the probe assembly and a first motor for moving the gripper assembly along the axis so that when the gripper assembly is moved while gripping the probe assembly, the probe assembly translates on the structure along the axis, and the rotation-imparting mechanism comprising a second motor that turns a pinion that is in mesh with a toothed segment that attaches to the stack via a mounting so that operation of the second motor rotates the structure and probe assembly about the axis.

2. An automated probe as set forth in claim 1 wherein the toothed segment comprises a ring gear.

3. An automated probe as set forth in claim 2 wherein the ring gear is fastened to an outer race of a slewing ring bearing assembly that has an inner race that is fastened to the structure to rotate within the outer race when the second motor rotates the probe assembly and the structure.

4. An automated probe as set forth in claim 3 including an outer cover enclosing the ring gear and the pinion.

5. An automated probe as set forth in claim 1 wherein the structure comprises opposite end walls joined together by trusses disposed to opposite lengthwise sides of the probe assembly.

6. An automated probe as set forth in claim 5 wherein the gripper assembly is mounted on a carrier of a linear actuator that contains, and is operated by the first motor, that has a length parallel to the axis of the probe assembly and that is disposed laterally between the trusses to a side of the probe assembly opposite the second motor.

7. An automated probe as set forth in claim 6 including a further gripper assembly that is stationarily mounted on the structure for association with the probe assembly to constrain the probe assembly against translation when gripping the probe assembly.

8. An automated probe for obtaining data at various locations in a stack flow through a stack, the automated probe comprising:
    a probe assembly having a sensing tip at one end;
    structure that supports a translation-imparting mechanism and a rotation-imparting mechanism for imparting translation and rotation respectively to the probe assembly to enable the probe assembly to obtain data about stack flow, rollers disposed on the structure for providing bearing support for the probe assembly while allowing the probe assembly to translate along an axis but constraining the probe assembly from turning on the structure about the axis, the translation-imparting mechanism comprising a gripper assembly that can grip and release the probe assembly and a first motor for moving the gripper assembly along the axis so that when the gripper assembly is moved while gripping the probe assembly, the probe assembly translates on the structure along the axis, and the rotation-imparting mechanism comprising a second motor that turns a pinion that is in mesh with a toothed segment that attaches to the stack via a mounting so that operation of the second motor rotates the structure and probe assembly about the axis, wherein the probe assembly comprises a square tube at one end of which the sensing tip is mounted, a wheel is coupled to an encoder and bears against a side of the square tube to rotate in correspondence with translation of the probe assembly and operate the encoder, and a sensor is associated with a linear actuator operated by the first motor to track translation of the linear actuator, allowing comparison of translation data from the encoder and translation data from the sensor to disclose slippage between the gripper assembly and the square tube when the linear actuator is translating the probe assembly.

9. An automated probe as set forth in claim 8 wherein the square tube is supported on and guided by sets of the rollers spaced along the length of the square tube.

10. An automated probe as set forth in claim 8 wherein the square tube comprises individual square tube sections spliced together end-to-end by smaller square tube splices.

11. An automated probe as set forth in claim 10 including pressure lines and electric wires running from the sensing tip through the square tube sections and square tube splices.

12. An automated probe as set forth in claim 9 further including rods extending between the sets of rollers to aid in guiding the square tube during passage of the square tube from a first set of rollers to a second set of rollers so that the square tube will align with the second set of rollers upon reaching the second set.

13. An automated probe as set forth in claim 10 further comprising fasteners fastening spliced-together square tube sections, the fasteners having shanks passing through clearance holes in the square tube sections and threading to a square tube splice that is inside spliced-together ends of the square tube sections, the fasteners further having heads that are exposed on the outside of the square tube sections and disposed at locations that are not gripped by the gripper assembly.

14. An automated probe as set forth in claim 1 in which the probe assembly comprises a square tube and the automated probe further comprises first and second sets of the rollers at locations that are spaced apart along length of the square tube for supporting and guiding the square tube, and rods extending between the first and second sets of rollers to aid in guiding the square tube during passage of the square tube from the first set of rollers to the second set of rollers so that the square tube will align with the second set of rollers upon reaching the second set.

15. An automated probe as set forth in claim 1 in which the first motor operates a linear actuator and the probe assembly comprises a tube at one end of which the sensing tip is mounted, and further comprising a tracking device that bears against the tube for tracking translation of the probe assembly and a sensor for tracking translation of the linear actuator to allow comparison of translation data from the tracking device and translation data from the sensor to disclose slippage between the gripper assembly and the tube when the linear actuator is translating the probe assembly.

16. An automated probe as set forth in claim 1 including a further gripper assembly that is stationarily mounted on the structure for association with the probe assembly to constrain the probe assembly against translation when gripping the probe assembly.

17. An automated probe as set forth in claim 1 including a motorized blower communicated through a port in a wall of the automated probe for pressurizing the interior to keep stack gases from intruding.

\* \* \* \* \*